United States Patent [19]

Kitamori et al.

[11] Patent Number: 4,738,536
[45] Date of Patent: Apr. 19, 1988

[54] METHOD FOR ANALYZING IMPURITIES IN LIQUID AND APPARATUS THEREFOR

[75] Inventors: Takehiko Kitamori; Shunsuke Uchida; Satoru Kawasaki; Masahiro Kondo, all of Hitachi, Japan

[73] Assignee: Hitachi, Ltd., Tokyo, Japan

[21] Appl. No.: 790,464

[22] Filed: Oct. 23, 1985

[30] Foreign Application Priority Data

Oct. 25, 1984 [JP] Japan ................................ 59-224947

[51] Int. Cl.$^4$ ............................................ G01N 21/00
[52] U.S. Cl. ...................................... 356/441; 73/657
[58] Field of Search ....................... 356/432, 436, 441; 73/53, 655, 656, 657

[56] References Cited

U.S. PATENT DOCUMENTS 4,581,939  4/1986  Takahashi ............................ 73/643

OTHER PUBLICATIONS

"Laser Induced Photoacoustic Spectroscopy of Some Rare Earth Ions in Aqueous Solutions", Analytical Chemistry, vol. 51, pp. 688–690, May 1979.
"Simultaneous Determination of Mixtures in Liquid by Laser-Induced Photoacoustic Spectroscopy", Analytical Chemistry, vol. 51, pp. 686–688, May 1979.
"Analysis of Turbid Solutions by Laser-Induced Photoacoustic Spectroscopy", Analytical Chemistry, vol. 52, pp. 650–653, 1980.
"Photoacoustic Effect as a Liquid Absorbance Detector", Applied Optics, vol. 19, No. 18, Sep. 15, 1980.

Primary Examiner—Eugene R. Laroche
Assistant Examiner—Robert J. Pascal
Attorney, Agent, or Firm—Antonelli, Terry & Wands

[57] ABSTRACT

A method for analyzing impurities in liquid and an apparatus therefor are disclosed, which are adapted to classify impurities contained in various liquids to be measured into soluble substance, insoluble substance and impurities in the form of bubbles and to measure their concentration separately; especially the impurities in liquid are analyzed by the method such that photoacoustic signals obtained by irradiating a liquid to be measured with intensity-modulated light are measured; the correlation between the modulation frequency of the intensity-modulated light (light modulation frequency) and the phase of the intensity-modulated light, with which the liquid to be measured is irradiated, as well as that of their photoacoustic signals are obtained; and impurities in the liquid to be measured are detected, while classifying them into soluble and insoluble ones and those in the form of bubbles on the basis of the information thus obtained: and the apparatus comprises a light source, at least one light modulator for transforming light from the light source into intensity-modulated light having a given constant frequency, at least one cell disposed at a position, where it is irradiated with the intensity-modulated light, and containing liquid to be measured, at least one phase detection device for detecting the phase of the photoacoustic signals coming from the cell, a calculating device for analyzing impurities in the liquid on the basis of this phase detection device, and a control device for controlling the modulation frequency (light modulation frequency) of the intensity-modulated light in the light modulator.

36 Claims, 7 Drawing Sheets

METHOD FOR ANALYZING IMPURITIES IN LIQUID AND APPARATUS THEREFOR

BACKGROUND OF THE INVENTION

This invention relates to a method and an apparatus for analyzing impurities in liquid, and more particularly to a method and an apparatus for analyzing impurities in various kinds of liquid such as ultra-pure water adapted to classify the impurities into soluble substance, insoluble substance and impurities in the form of bubbles, and to measure their concentrations separately.

It is known that photoacoustic spectroscopy is useful for a highly sensitive spectroscopic analyzing method, when it is applied to liquid samples and used as a colorimetric analyzing apparatus. Shohei Oda, Tsuguo Sawada and Hitoshi Kamada have reported in an article entitled "Determination of Ultra Trace Cadmium by Laser-Induced Photoacoustic Absorption Spectrometry", Analytical Chemistry, Vol. 50, p. 865 (1978), that cadmium can be analyzed down to 12 ppt in the form of a complex salt with dithizone by means of a photoacoustic analyzing apparatus. Further, Shohei Oda, Tsuguo Sawada, Toyohiko Moriguchi and Hitoshi Kamada have reported that when the photoacoustic analyzing method is applied to suspension of barium sulfate its detection limit is 30 ppb in an article entitled "Analysis of Turbid Solution by Laser-Induced Photoacoustic Spectroscopy", Analytical Chemistry, Vol. 52, p. 650 (1980). It has been shown in this example that the calibration curve of the suspension doesn't depend on the diameter of particles, when light modulation frequency is set at 33 Hz. That is, it has been shown that the photoacoustic analyzing method has a characteristic that it is not influenced by the diameter of suspended particles.

However, on the other hand, it has been verified by the present inventors that the phase of photoacoustic signal depends on the diameter of suspended particles and that the diameter and the concentration of suspended particles can be measured by the photoacoustic analyzing method.

In this way, it has been verified that the photoacoustic analyzing method can be applied to highly sensitive analyzing and is useful not only for analysis of true solutions but also for that of suspensions. However, no technique has been known, which is adapted to measure separately not only insoluble impurities but also soluble ones (impurities in the form of ions) in liquid, utilizing such characteristics as described above of the photoacoustic analyzing method. This is because theoretical relations between measurement conditions such as the light modulation frequency for the photoacoustic analyzing apparatus and information obtained under those conditions are not known.

Furthermore, the amount of impurities contained in ultra-pure water is on the order of ppt's and this concentration level is below the lower detection limit of the conventional analyzing method such as chromatography, colorimetry, etc. Consequently, it is difficult to apply the prior art analyzing methods to analysis of impurities in ultra-pure water.

As stated above, none of the conventional impurity analyzing methods is adapted to analyze any kind of impurities such as fine particles whose concentration is very low (insoluble substance), substance in the form of ions (soluble substance), and further impurities in the form of bubbles. Furthermore there exists no apparatus for analyzing impurities in liquid permitting not only these analyses but alsl on-line measurements.

SUMMARY OF THE INVENTION

The object of this invention is to provide a method for analyzing impurities in liquid and an apparatus therefor, which are adapted to classify impurities in a liquid to be measured into soluble and insoluble impurities as well as those in the form of bubbles, and to measure their concentrations separately.

In one aspect of this invention, a method for analyzing impurities in liquid is carried out by measuring a photoacoustic signal obtained by irradiating onto a liquid to be measured an intensity-modulated light, obtaining the relationship between the modulation frequency of the intensity-modulated light (light modulation frequency) and the phase of the photoacoustic signal, and determining the kinds of impurities in the liquid, as classified into soluble and insoluble and those in the form of bubbles on the basis of the information thus obtained.

In another aspect of this invention, there is provided an apparatus for analyzing impurities in liquid comprising a light source; at least one light modulator for transforming light from the light source into intensity-modulated light having a given constant frequency; at least one cell disposed at a position where it is irradiated with the intensity-modulated light and containing therein liquid to be measured; at least one phase detection device for detecting the phase of the photoacoustic signals coming from the cell; a calculating device for analyzing impurities in the liquid on the basis of information obtained by the phase detection device; and a control device for controlling the modulation frequency (light modulation frequency) of the intensity-modulated light derived from the light modulator.

According to this invention, a photoacoustic signal obtained by irradiating onto a liquid sample such as ultra-pure water an intensity-modulated light is measured and the kinds of impurities in the liquid sample as classified into soluble and insoluble substances and substance in the form of bubbles and the concentrations thereof are determined on the basis of the relation between the modulation frequency (light modulation frequency) of the intensity-modulated light and the phase, as well as the intensity, of the photoacoustic signal.

Next, explanation will be made of the construction of the apparatus for measuring the kinds of impurities in liquid as classified into soluble and insoluble ones and those in the form of bubbles and the concentrations thereof on the basis of the relationship between the phase and the intensity of the photoacoustic signal and the light modulation frequency or the relationship between the phase set by the phase detection device for the photoacoustic signal and the light modulation frequency referring to FIG. 1 and Table 1.

TABLE 1

| | Measurement conditions and information | | |
|---|---|---|---|
| Light modulation frequency $\omega$ | Phase of lock-in amp. $\theta$ | Information source | Information |
| $\omega \ll \dfrac{3h}{\rho_s C_{Ps} d_c}$ | $\theta = \phi_Q$ | S | Total amount of impurities |
| $\omega \geq \dfrac{3h}{\rho_s C_{Ps} d_c}$ | $\theta = \phi_Q + \phi_D$ | S | Amount of insoluble impurities |
| | | $\phi_D$ | Center value of particle diameters |
| | $\theta = \phi_Q$ | S | Amount of soluble impurities |
| | $\theta = 0$ | S | Mixing of bubbles |

1. Explanation of notation $\rho_s$: specific weight of particles
$C_{Ps}$: specific heat of particles
h: heat transfer coefficient from particles to medium
$d_c$: lower detection limit of radius of particles
$\phi_Q$: phase delay due to propagation of photoacoustic signals
$\phi_D$: phase delay due to delay in time necessary for heat evacuation after incidence of light to particles
S: intensity of photoacoustic signals The principle of this invention is based on the fact that the relation between the light modulation frequency and the phase of the photoacoustic signals varies depending on the property of impurities, as indicated in Table 1.

Hereinbelow, the principle on the basis of which the relation between the measurement conditions and information, as indicated in Table 1, can be obtained will be explained, according to the theory of the inventors of this invention on generation, propagation and detection of photoacoustic signals. Impurities absorbing periodically intensity-modulated light produce periodically heat by nonradiative processes. This heat induces periodical thermal expansion of the medium and as the result generates acoustic waves. The generated acoustic waves, i.e. photoacoustic signals are represented by $P(\boldsymbol{\alpha}, t)$, where $\boldsymbol{\alpha}$ represents a vector in an arbitrarily set spatial coordinate system and t represents time. The photoacoustic signals can be described as acoustic waves by the following wave equation;

$$\left(\nabla_{\boldsymbol{\alpha}}^2 - \frac{1}{C^2}\frac{\partial}{\partial t}\right)P(\boldsymbol{\alpha}, t) = -\frac{\beta}{C_p}\frac{\partial}{\partial t}H(\boldsymbol{\alpha}, t), \quad (1)$$

where C is the sound velocity, $\beta$ is the thermal expansion coefficient of the medium, $C_P$ is the specific heat of the medium, $H(\boldsymbol{\alpha}, t)$ represents the time and spatial distribution of heat generated by the nonradiative processes, and $\nabla_{\boldsymbol{\alpha}}$ is a differential operator with respect to the vector $\boldsymbol{\alpha}$. The solution of this wave is in general given by the following equation;

$$P(\boldsymbol{\alpha}, t) = F^{-1}\left[-\frac{\beta}{C_P}\int_{\boldsymbol{\alpha}'}\bar{H}(\boldsymbol{\alpha}', \omega) G(\boldsymbol{\alpha}|\boldsymbol{\alpha}')d_{\boldsymbol{\alpha}'}\right] \quad (2)$$

where F is a Fourier transformation operator; $\bar{H}(\boldsymbol{\alpha}', \omega)$, etc. are Fourier images of a function $H(\boldsymbol{\alpha}, t)$; and $G(\boldsymbol{\alpha}|\boldsymbol{\alpha}')$ is a Green function determined by the boundary conditions given by the structure, materials, etc. of the cell. The concrete representation of the photoacoustic signals $P(\boldsymbol{\alpha}, t)$ is given by the structure and the materials of the cell as well as the concrete representation of the function $H(\boldsymbol{\alpha}, t)$.

In the case where the impurities are soluble, since the solution is a true solution, the spatial distribution of $H(\boldsymbol{\alpha}, t)$ coincides with the spatial distribution of the projected light. Further, in the case where the nonradiative relaxation time of the impurities is sufficiently short and negligeable with respect to the period of the light modulation, the time distribution of $H(\boldsymbol{\alpha}, t)$ coincides with the time distribution of the projected light. Consequently, the following equation can be obtained;

$$H(\boldsymbol{\alpha}, t) = \alpha I_0 P_u(\boldsymbol{\alpha})M(t) \quad (3),$$

where $\alpha$ is an absorption coefficient of the solution; $I_0$ is the intensity of the projected light; $R(\boldsymbol{\alpha})$ represents the spatial distribution of the projected light; and $M(t)$ represents the time distribution of the projected light and is called the modulation function. Using Eqs. (2) and (3), $P_1(\boldsymbol{\alpha}, t)$ representing the photoacoustic signals for soluble impurities is given by a representation (4) as follows;

$$P_1(\boldsymbol{\alpha}, t) = F^{-1}\left[\frac{\alpha\beta}{C_p}I_0 i\omega M(\omega)\int\boldsymbol{\alpha}' R(\boldsymbol{\alpha}')G(\boldsymbol{\alpha}|\boldsymbol{\alpha}')d\boldsymbol{\alpha}'\right] \quad (4)$$

$$= \frac{\alpha\beta}{C_p}I_0 F^{-1}[i\omega M(\omega)\int\boldsymbol{\alpha} R(\boldsymbol{\alpha})G(\boldsymbol{\alpha}|\boldsymbol{\alpha})d\boldsymbol{\alpha}]$$

Next, in the case where the impurities are insoluble, a representation for the photoacoustic signals can be deduced as follows. As indicated in FIG. 2, an impurity particle 41 absorbs light 42 and releases heat produced by a radiationless transition in the form of a thermal flux 43 in the medium. Representing this thermal flux by J, J is given by the following equation, which is produced according to a temperature field $T(\rho, t)$ formed around the impurity particle;

$$J = -\lambda\vec{n}\cdot\nabla_\rho T(\rho, t) \quad (5),$$

where $\rho$ indicates a vector representing the position of the impurity particle in the coordinate system; $\lambda$ is the heat conduction coefficient of the medium; and $\vec{n}$ indicates the normal vector. The temperature field $T(\rho, t)$ can be obtained by using the following heat equations;

$$\left(\nabla_\rho^2 - \frac{1}{K_s^2}\frac{\partial}{\partial t}\right)T(\rho, t) = -\frac{\alpha_S}{\lambda_S}R(\boldsymbol{\alpha})M(t) \quad (6)$$

$(\rho \epsilon V)$ $$\left(\nabla_\rho^2 - \frac{1}{K^2}\frac{\partial}{\partial t}\right)T(\rho, t) = 0 \quad (7)$$

-continued $$(\rho \oplus \mathbf{v})$$

where K is the heat diffusion coefficient; $\mathbf{v}$ indicates the region inside of the impurity particle; and the characters with suffix S indicate that the properties represented by the respective characters are concerned with the impurity particle. In the case where impurity particles are distributed uniformly in the cell, $H(\varkappa, t)$ can be obtained by using the following equation;

$$H(\varkappa, t) = H \int_S - \overline{\lambda \vec{n}} \cdot \nabla_\rho T(\rho, t) d\rho \tag{8}$$

where N is the density in number of the impurity particles and it is related to the impurity concentration C by the following equation;

$$C = N/V_\sigma S \tag{9}$$

where $\sigma$ indicates the density and V represents the volume of the impurity particles. $\int_S$ in Eq. (8) indicates integration over the surfaces of the impurity particles. In the case where the impurity particles are sufficiently small and the temperature of all the impurity particles varies uniformly, by resolving Eqs. (5) to (9), $\bar{H}(\varkappa, \omega)$ is represented by Eq. (10) as follows;

$$\bar{H}(\varkappa, \omega) = -\frac{\lambda}{\lambda_S} \frac{C}{\sigma_S} \alpha_S I_0 R(\varkappa) \bar{M}(\omega) \times \frac{\frac{S}{V} h}{\sigma_S C_{P_S} i\omega + \frac{S}{V} h}. \tag{10}$$

Substituting $\bar{H}(\mathbf{R}, \omega)$ of Eq. (10) for Eq. (2), the photoacoustic signals $P_2(\varkappa, t)$ coming from the impurity particles can be obtained by using the following equation;

$$P_2(\varkappa, t) = \frac{\beta}{C_P} \frac{\lambda}{S} \frac{C}{\sigma_S} \alpha_S I_0 F^{-1} [\bar{D}(\omega) \bar{M}(\omega) \times i\omega \int \varkappa, R(\varkappa') G(\varkappa | \varkappa') d\varkappa'], \tag{11}$$

where $$D(\omega) + \frac{\frac{S}{V} h}{\sigma_S C_{P_S} i\omega + \frac{S}{V} h}. \tag{12}$$

When the modulation function $\bar{M}(t)$ is a sinusoidal function having an angular frequency $\omega_0$, since $$\bar{M}(\omega) = \delta(\omega - \omega_0) \tag{13}$$

Eqs. (4) and (11) can be transformed into the following equations;

$$P_1(r, t) = \frac{\beta}{C_P} \alpha I_0 Q(r, t) e^{i\omega_0 t}, \tag{14}$$

$$P_2(r, t) = -\frac{\beta}{C_P} \frac{\lambda}{\lambda_S} \frac{C}{\sigma_S} \alpha_S I_0 \bar{D}(\omega_0) Q(r, t) \cdot e^{i\omega_0 t} \tag{15}$$

where $$Q(r, t) = i\omega_0 \int_r R(r') G(r|r') dr' \tag{16}$$

When the diameter of impurity particles is nearly zero, Eq. (15) coincides with Eq. (14) and the photoacoustic signals from a liquid containing insoluble impurities become identical to those from a true solution. In order to make the intensity and the phase of the photoacoustic signals more distinctive, Eqs. (14) and (15) may be represented in a polar coordinate system, as follows;

$$P_1(r, t) = \frac{\beta}{C_P} \alpha I_0 Q e^{i(\omega_0 t - \phi_Q)} \tag{17}$$

$$P_2(r, t) = \frac{\beta}{C_P} \frac{\lambda}{\lambda_S} \frac{C}{\sigma_S} \alpha_S I_0 \bar{D} Q e^{i(\omega_0 t - \phi_D - \phi_Q)}, \tag{18}$$

where $$Q = |Q(r, t)| \tag{19}$$

$$\bar{D} = |\bar{D}(r, t)| \tag{20}$$

$$\phi_Q = \tan^{-1} \frac{I_m Q(r, A)}{R_e Q(r, t)} \tag{21}$$

$$\phi_D = \tan^{-1} \frac{\sigma_S C_{P_S} V}{hS} \omega_0. \tag{22}$$

Consequently, $\phi_Q$ represents the phase delay due to propagation of the photoacoustic signals and $\phi_D$ indicates the phase delay of the photoacoustic signal due to the time interval required for release of heat produces in the impurity particles.

By using Eqs. (12) to (22), the conditions for the classification of the impurities and the measurement of their concentrations, as indicated in Table 1, can be obtained. At first, in the case where the light modulation angular frequency $\omega_0$ sufficiently satisfies $$\sigma_S C_{P_S} \omega_0 << S/Vh \tag{23}$$

and the following equation is valid;

$$\bar{D}(\omega_0) = 1,$$

it can be seen from Eq. (18) that the intensity of the photoacoustic signal is independent of the size of the impurity particles. Furthermore, in this case, from Eq. (22)

$$\phi_D = 0$$

can be obtained. Thus, only $\phi_Q$ gives the phase delay of the photoacoustic signal in Eqs. (17) and (18) so that the phase of the photoacoustic signal from the liquid containing insoluble impurities coincides with that from a solution containing soluble impurities. Since the photoacoustic signal is an acoustic wave having linear characteristics, the principle of superposition is applied to the signal. Under these conditions, the intensity of the photoacoustic signal corresponds to the sum of the concentration of soluble impurities and that of insoluble ones and the resultant phase is $\phi_Q$. Therefore, when the phase $\theta$ of the lock-in amplifier for the photoacoustic signal is set at $$\theta = \phi_Q,$$

the intensity of the phase-detected photoacoustic signal represents the total amount of impurities contained in the solution. On the other hand, when $\omega_0$ satisfies $$\sigma_S C_{Ps} \omega_0 \gtrsim S/Vh \qquad (24)$$

and $\phi_D$ is distinguishable from $\phi_Q$, it can be understood that the insoluble impurities can be measured separately from soluble ones. In this case, the size of the impurity particles can be known from Eq. (22) and thus, in the case where the impurities particles can be assumed to be spherical, since $S=4\pi d^2$ and $V=4/3\pi d^3$ in Eq. (22), the radius d of the impurity particles is given by $$d = \frac{3h \tan \phi_D}{\sigma_S C_{Ps} \omega_0} \qquad (25)$$

In addition, for the conditions given by Eqs. (23) and (24) the following relationship is valid;

$$S/V h = 3h/d \qquad (26).$$

This means that, in the case where $\phi_D=0$, even if the projected light is modulated with a light modulation frequency satisfying Eq. (24), the impurities are not particles but all of them are soluble.

In the case where the impurities are in the form of bubbles, the projected light is refracted by bubbles, changes its path and can enter directly the detector. In this case, the incident light produces photoacoustic signals of the detector itself. However, since the light velocity is much greater than the sound velocity, the phase of the photoacoustic signal is zero. Consequently, it is possible to measure bubbles, distinguishing them from soluble and insoluble impurities.

DESCRIPTION OF THE PREFERRED EMBODIMENTS

Figure 1:
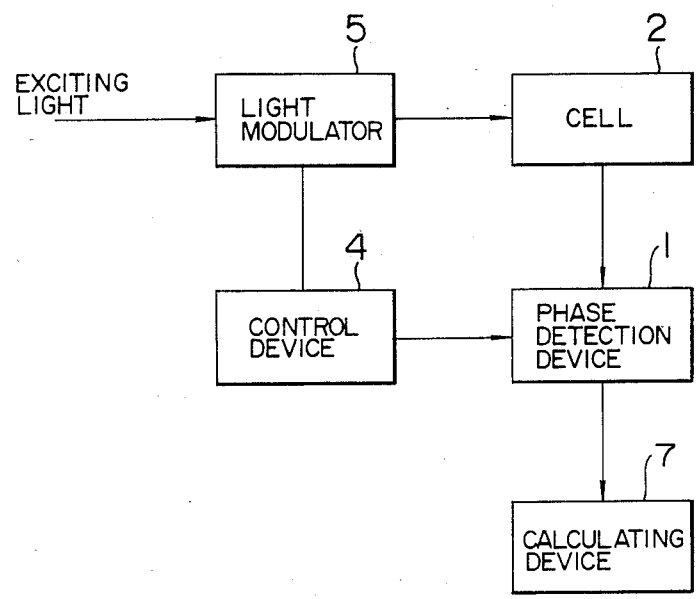
FIG. 1 is a block diagram showing the basic structure of this invention.
Figure 2:
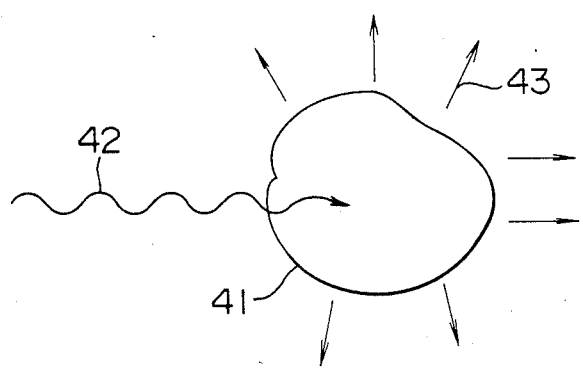
FIG. 2 is a schematic diagram for explaining the process of absorbing light and releasing heat.

Hereinbelow the embodiments of this invention will be explained, referring to the drawing.

FIG. 1 is a block diagram showing the basic structure of this invention. Light emitted by a light source enters a light modulator 5, in which the incident light is transformed into intensity-modulated light, whose intensity varies at a constant frequency, and a cell 2 containing a liquid sample to be measured is irradiated with this intensity-modulated light. The reference numeral 1 represents a phase detection device having functions to receive photoacoustic signals obtained at the cell 2 and measure the phase and the intensity of the photoacoustic signal or to take out only the photoacoustic signal which has a given phase from the received signal and measure its intensity. The reference numeral 4 indicates a control device, which sets the light modulation frequency in the light modulator 5 and also the phase in the phase detection device 1. The reference numeral 7 represents a calculating device, which classifies impurities contained in the liquid sample, calculates their amount (concentration), and displays results, if necessary, on the basis of information obtained by the phase detection device 1.

Figure 3:
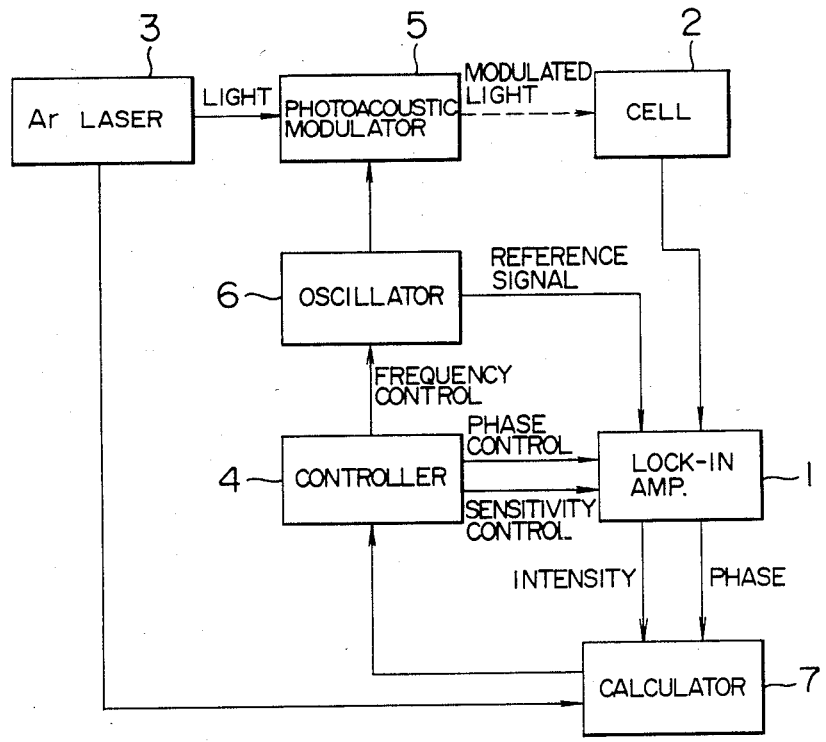
FIG. 3 is a block diagram showing a first embodiment of this invention.

FIG. 3 shows a first embodiment of an apparatus for analyzing impurities in liquid, in which the light modulation frequency can be set at any desired value and a lock-in amplifier is used as the phase detection device 1 for detecting the phase of the photoacoustic signals, the phase and the sensitivity of the lock-in amplifier 1 also able to be set at any desired value. The light modulation frequency as well as the phase and the sensitivity of the lock-in amplifier are controlled by the control device coupled with a calculator on the basis of Table 1. In this embodiment a sample such as ultra-pure water, etc. is prepared and filled in a sealed type cell 2 and the photoacoustic signal derived from the sample is measured. In this apparatus an Ar laser device is used as the light source 3 and a light beam of 2.6 W having an oscillation line of 488 nm is utilized as exciting light. In this apparatus, the light modulation frequency is set at 80 Hz for low frequency modulation and at 410 kHz for high frequency modulation. These light modulation frequencies sufficiently satisfy Eqs. (23) and (24), respectively, for particles of silicon dioxide having a radius of 1 $\mu$m in water. Once the low frequency modulation is selected, the phase of the lock-in amplifier 1 is set automatically at a value as mentioned before by the controller (control device) 4 and measures only the intensity of the photoacoustic signal. In this way, the total amount of impurities (concentration) in the sample can be obtained. In this case, the lower detection limit of the light-absorption coefficient is about $10^{-8}$/cm. Further, when the impurities are silicon dioxide particles, they can be measured down to about 20 ppt. When the measurement of the total amount of impurities is terminated, the light modulation frequency is set automatically at the high frequency side and the lock-in amplifier acts as a phase detector. In this case, for a particle radius of 1 $\mu$m the phase is 45 degrees and the smallest measurable value of the phase detector of 0.5 degree corresponds to a particle radius of about 0.1 $\mu$m.

In addition, in the embodiment shown in FIG. 3, the reference numeral 5 is the photoacoustic modulator transforming light coming from the Ar laser 3 into modulated light; 6 is the oscillator feeding the lock-in amplifier 1 and the photoacoustic modulator 5 with signals; and 7 represents the calculator (calculating device). Further, since a photoacoustic modulator 5 is used as the light modulator 5, an oscillator 6 is disposed, which drives the modulator.

Figure 4:
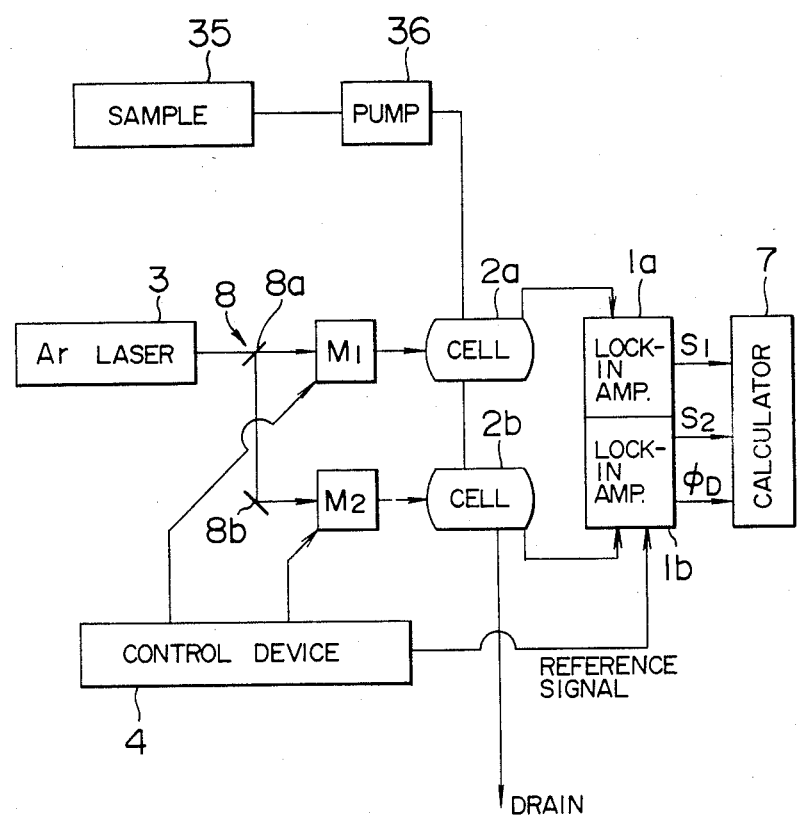
FIG. 4 is a system diagram showing a second embodiment of this invention.
Figure 5:
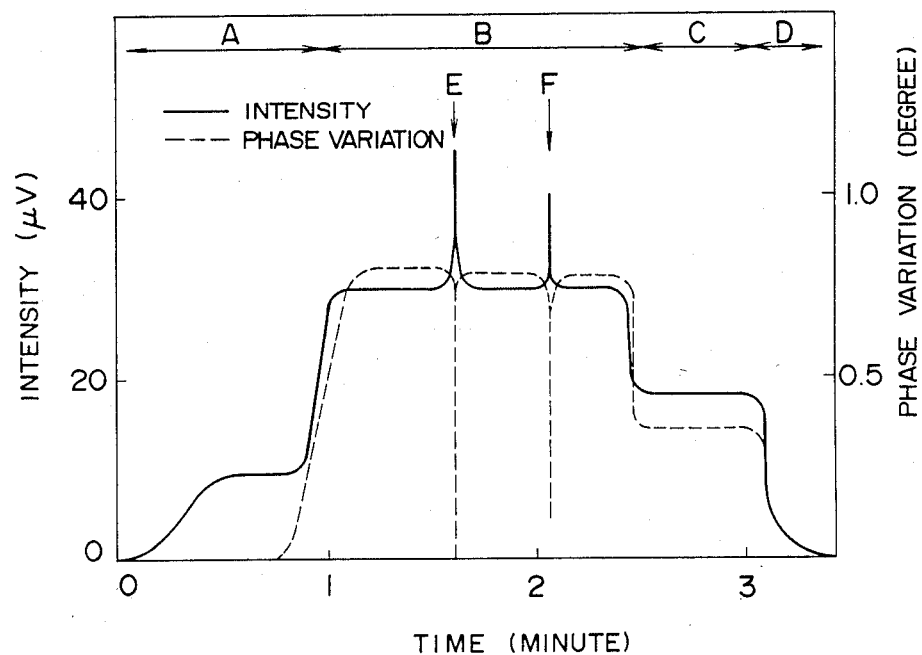
FIG. 5 shows graphs indicating measurement examples obtained by using the apparatus indicated in FIG. 4.

Next, a second embodiment of the apparatus according to this invention will be explained, referring to FIG. 4. In this embodiment, flow type cells are used and 2 sets of light modulators $M_1$, $M_2$, cells $2a$, $2b$ combining the same sample and lock-in amplifiers $1a$, $1b$ are disposed. These 2 sets are adjusted for different measurement conditions. The light source 3 is an Ar laser device having an output 20 W. The light modulator $M_1$ is set at 80 Hz and $M_2$ at 410 kHz. The setting value of these light modulation frequencies can be varied by the control device 4. The lock-in amplifier $1a$ measures the intensity $S_1$ and $1b$ measures variations in phase $\phi_D$ and the intensity $S_2$. The measured values $S_1$, $S_2$ and $\phi_D$ are processed by a calculator 7. Further, in the figure, the reference numeral 8 indicates a light distributing device disposed between the light source 3 and the light modulators $M_1$, $M_2$, that is, $8a$ is a beam splitter, which directs the incident light beam toward 2 directions, and $8b$ is a mirror, which reflects the incident beam. The liquid sample 35 flows successively through the cells $2a$ and $2b$ by means of a pump 36. FIG. 5 shows an example of measurements according to this embodiment. The figure shows that soluble impurities of 20 ppb flows in the region A and impurities of 60 ppt having a particle radius of 0.3 $\mu$m are detected in the region B. In the region C impurities of 30 ppt in the form of particles having a particle radius of 0.15 $\mu$m are detected. In the region D no impurities are detected. The relationship between the intensity of signals and the concentration in this apparatus is as follows;

Soluble impurity concentration = signal intensity
$(\mu V) \times 2(ppb/\mu V)$             (27)

Insoluble impurity concentration = signal intensity
$(\mu V) \times 2(ppt/\mu V)$             (28)

In this case, for the soluble impurities, calculations were effected, assuming that the molecular light absorption coefficient is 10 (mol. cm$^{-2}$).

Furthermore, it can be seen that at E and F bubbles are detected.

Figure 6:
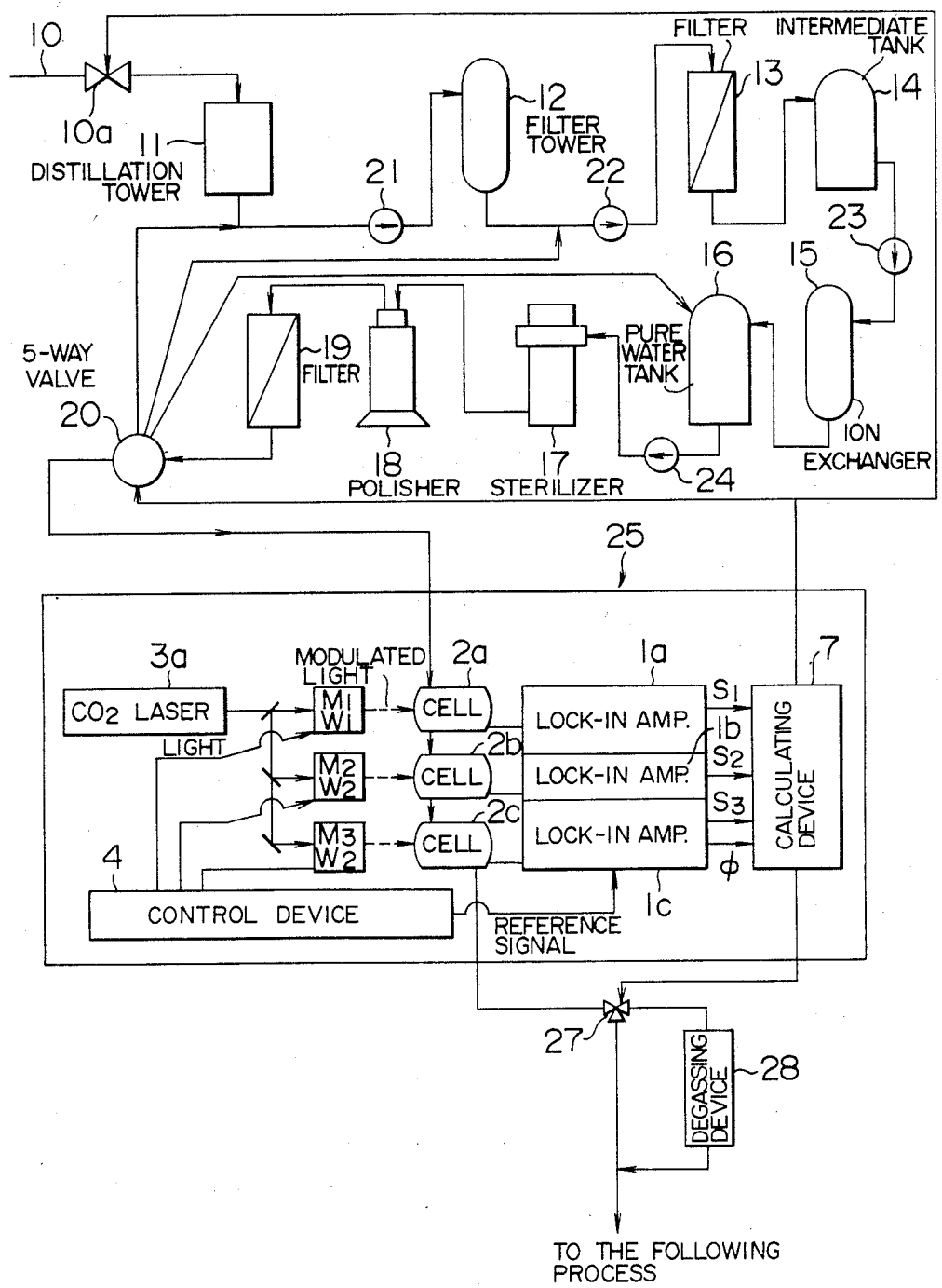
FIG. 6 is a system diagram showing a third embodiment of this invention.

FIG. 6 shows a third embodiment of this invention, in which the method according to this invention is applied to an ultra-pure water production apparatus.

In the figure, the reference numeral 10 indicates a raw water supply line for feeding a distillation tower 11 with raw water such as city water; 12 is an activated charcoal filter tower for eliminating organic impurities; 13 is an inverse osmotic membrane module for eliminating particles, electrolyte, etc.; 14 is an intermediate tank; 15 is an ion exchange resine tower for eliminating electrolyte, etc.; 16 is a pure water tank for storing produced pure water (specific resistance greater than 1-10 M$\Omega$cm); 17 is an ultra-violet ray sterilizer for sterilizing bacteria; 18 is a polisher for eliminating electrolyte; and 19 is an ultra-filtration membrane module for eliminating fine particles. This ultra-filtration membrane module 19 feeds a 5-way valve 20 with ultra-pure water, whose specific resistance is greater than 17-18 M$\Omega$cm and in which the number of fine particles larger than 0.1-0.2 $\mu$m is smaller than 50/cc and that of living bacteria is smaller than 0.1/cc. Further, in the figure, 21 to 24 represent water sending pumps or pressuring pumps.

Produced ultra-pure water is supplied successively from the 5-way valve 20 to the cells $2a$, $2b$ and $2c$ of the apparatus 25 for analyzing impurities. $3a$ indicates a light source utilizing a high energy $CO_2$ laser; $9a$ is a beam splitter; $9c$ is a half mirror; $9b$ is a mirror; $M_1$, $M_2$ and $M_3$ are light modulators; $1a$, $1b$ and $1c$ are lock-in amplifiers; 4 is a controlling device controlling the light modulators $M_1$ to $M_3$ and the lock-in amplifiers $1a$ to $1c$; and 7 is a calculating device for classifying impurities into various sorts and calculating their concentration on the basis of information coming from the lock-in amplifiers $1a$ to $1b$. This calculating device 7 is provided also with the function to control a valve $10a$ mounted on the raw water supply line 10, the 5-way valve 20 and another valve 27, depending on analysis results of the produced ultra-pure water. The light modulation frequency $\omega_1$ of the light modulator $M_1$ is set at 33 Hz and the light frequencies $\omega_2$ and $\omega_3$ of the light modulators $M_2$ and $M_3$, respectively, are set at 4 MHz. The phase of the lock-in amplifiers $1a$ and $1b$ is set at $\phi_D = 48°$ obtained previously experimentally. The total amount of impurities and the amount of soluble impurities are measured on the basis of the intensity of the photoacoustic signals $S_1$ and $S_2$, respectively. The lock-in amplifier $1c$ measures the phase $\phi$ and the intensity $S_3$ of the photoacoustic signals. Thus, the main radius of particles of insoluble impurities is obtained from the phase $\phi$ and the concentration of the insoluble impurities is calculated on the basis of the intensity $S_3$. The signals coming from the lock-in amplifiers $1a-1c$ are directly inputted to the calculating device 26 and control the 5-way valve 20 described above as follows.

If $S_1 > 100$ $\mu$V→Stop of water supply (the valve $10a$ is closed.)

If $S_2 > 50$ $\mu$V→Redoing of purification after the inverse osmotic membrane module 13 or the ion exchange resine tower 15.

If $S_3 > 50$ $\mu$V and at the same time $\phi > 0.5°$→Redoing of purification by returning water to the upstream of the pure water tank 16 or the ultra-filtration membrane module.

For the above described conditions it is assumed that purification is repeated, if the amount of soluble impurities is greater than about 1 ppb and if the amount of insoluble impurities is greater than 10 ppt and at the same time their particle radius is greater than 0.3 $\mu$m. Further, when the phase of the lock-in amplifier $1c$ is 0, since bubbles are mixed in the ultra-pure water, the valve 27 is commuted to the side of a degassing device 28 and after having degassed the ultra-pure water, it is supplied to a use point for example for semiconductor production.

Furthermore, although all the produced ultra-pure water passes through the apparatus for analyzing impurities 25 in this embodiment, in the case where the capacity of the pure water production apparatus is large, the analyzing apparatus 25 can also be constructed such that only a part of the produced ultra-pure water is bypassed therethrough.

Figure 7:
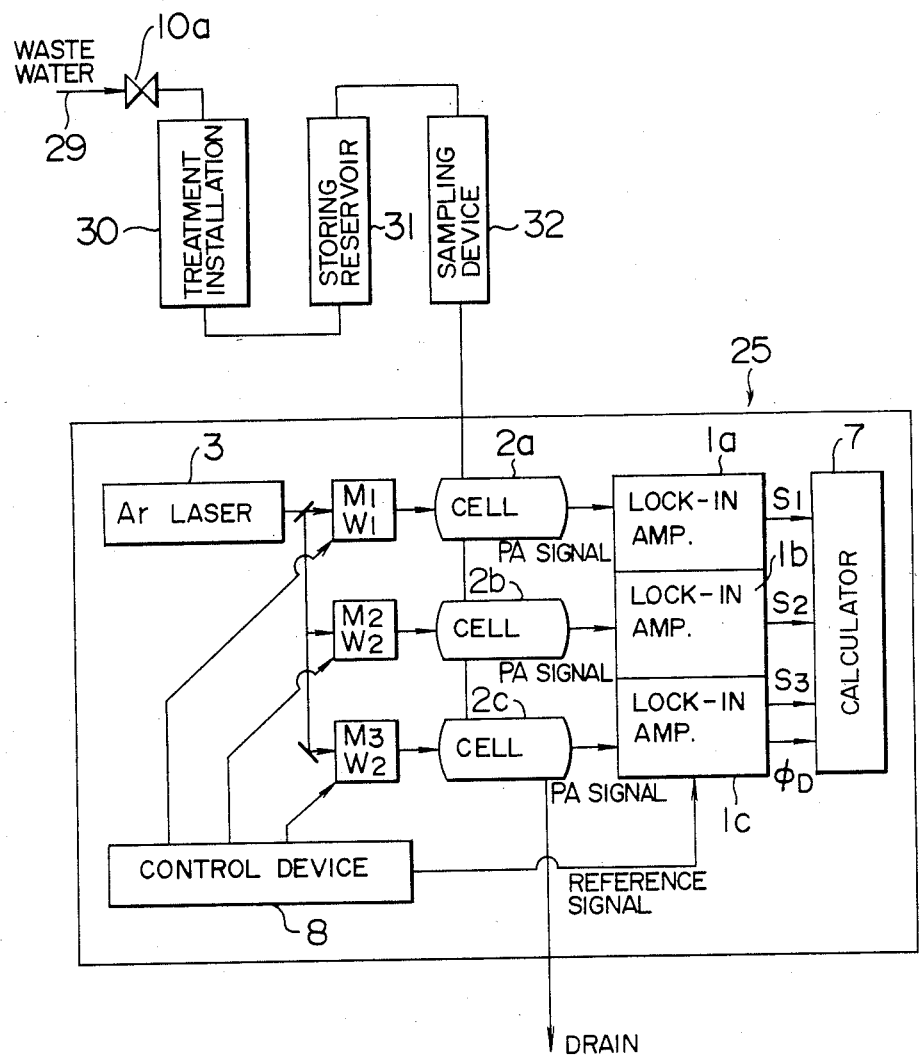
FIG. 7 is a system diagram showing a fourth embodiment of this invention.

FIG. 7 shows a fourth embodiment of this invention, in which an apparatus for analyzing impurities according to this invention is applied to industrial waste water. In the figure, the reference numerals, which are used also in FIG. 4 or FIG. 6, represent identical or corresponding parts.

The reference numeral 29 indicates a waste water ejecting line; 30 is a waste water treatment installation; 31 is a storing reservoir; and 32 is a sampling device. Samples taken in this sampling device 32 are supplied successively to the cells $2a$, $2b$ and $2c$ of the apparatus for analyzing impurities. In this embodiment an Ar laser device of 5 W is used as the light source 3. The other conditions are identical to those described for the embodiment illustrated in FIG. 6. The photoacoustic signals (PA signals) coming from the cells $2a$ to $2c$ are inputted to the lock-in amplifiers $1a$ to $1c$, respectively, and the intensities $S_1$ to $S_3$ of the photoacoustic signals from the lock-in amplifiers $1a$ to $1c$ as well as the phase $\phi_D$ of the photoacoustic signals from the lock-in amplifier $1c$ are inputted to the display-recording device (calculating device) 7. The samples, which have passed through the cells 2a to 2c, are ejected by the drain.

Figure 8:
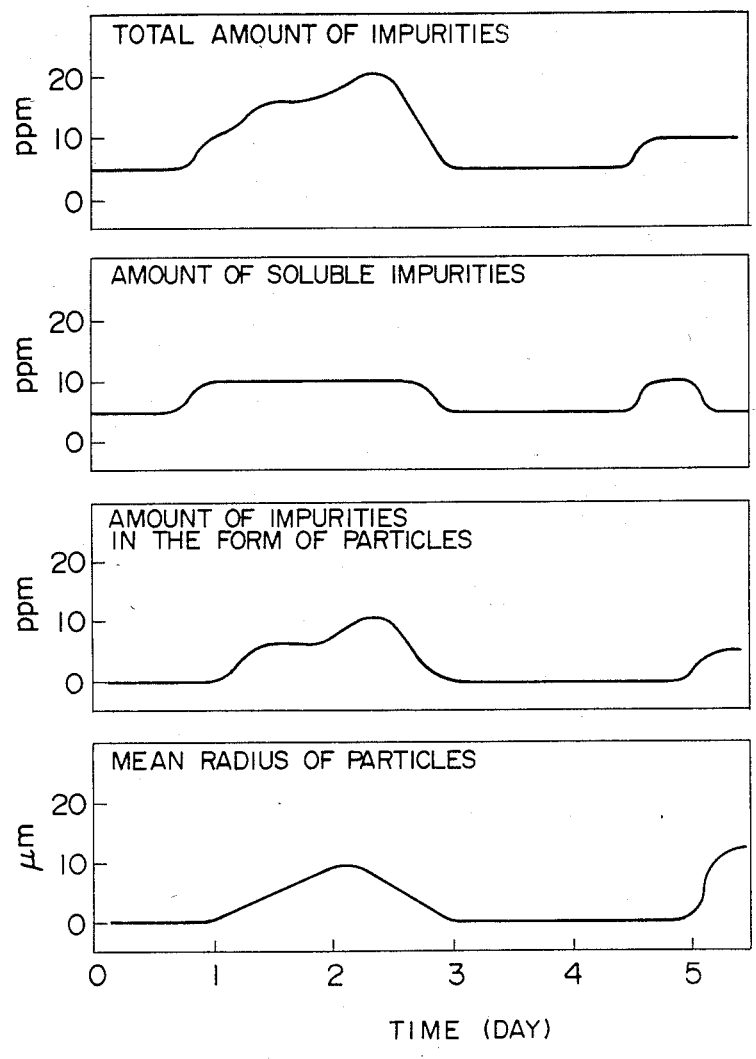
FIG. 8 shows graphs indicating measurement examples obtained by using the apparatus indicated in FIG. 7.

FIG. 8 shows a result obtained by analyzing industrial waste water by means of the apparatus indicated in FIG. 7.

As indicated above, the apparatus for analyzing impurities according to this invention can be applied to the case where samples to be analyzed are turbid and suspended.

According to the above-described embodiments of this invention the following effects can be obtained.

(1) It is possible to classify impurities into soluble and insoluble ones as well as bubbles in liquid and to measure their concentration separately.

(2) It is possible to analyze an extremely small amount of impurities (order of ppt), because the photoacoustic spectroscopic method is applied to the detection.

(3) It is possible to analyze turbid samples, because the photoacoustic spectroscopic method is utilized for the detector.

(4) It is possible to monitor impurities in liquid, because on-line measurement can be effected. Consequently, when this method is applied to the water quality control of ultra-pure water, on-line control of the water quality can be effected and production yield in semiconductor process and genetic engineering plants is increased.

As explained above, according to this invention, since impurities in liquid are analyzed on the basis of information on the modulation frequency of intensity-modulated light, with which liquid samples are irradiated, the relationship between the phase of the intensity-modulated light and that of the photoacoustic signal, and the intensity of the photoacoustic signal, it is possible to classify impurities in liquid into soluble and insoluble ones and those in the form of bubbles and also to measure their concentration separately.

What is claimed is:

1. A method for analyzing impurities in a liquid comprising the steps of:

modulating light at a constant modulation frequency $\omega$ so as to generate intensity-modulated light having an intensity which varies at a constant frequency;

irradiating a liquid to be measured with said intensity modulated light so as to induce impurities in said liquid to generate photoacoustic signals in said liquid;

detecting the phase of said photoacoustic signals;

obtaining relationships between the modulation frequency of said intensity modulated light, the phase of said intensity modulated light, and the phase of said photoacoustic signals; and analyzing and classifying said impurities as soluble impurities, insoluble impurities and bubbles, based on said obtained relationships;

wherein, when the total number of impurities in the liquid are to be measured, the light modulation frequency $\omega$ is determined such that it satisfies:

$$\omega << 3h/\rho_S C_{P_S} d_c,$$

where $\rho_S$ represents the specific weight of the impurities to be measured; $C_{P_S}$ represents the specific heat of the impurities; $d_c$ represents the radius of the impurities; and h represents the heat transfer coefficient from the impurities to the liquid;

wherein the phase $\theta$ of a phase detection device for detecting the phase and intensity of the photoacoustic signals is set such that it satisfies:

$$\theta = \phi_Q,$$

where $\phi_Q$ indicates a phase delay due to propagation of the photoacoustic signals; and wherein the total amount of impurities in the liquid is calculated on the basis of the intensity of the photoacoustic signals.

2. A method for analyzing impurities in a liquid comprising the steps of:

modulating light at a constant modulation frequency $\omega$ so as to generate intensity-modulated light having an intensity which varies at a constant frequency;

irradiating a liquid to be measured with said intensity modulated light so as to induce impurities in said liquid to generate photoacoustic signals in said liquid;

detecting the phase of said photoacoustic signals;

obtaining relationships between the modulation frequency of said intensity modulated light, the phase of said intensity modulated light, and the phase of said photoacoustic signals; and analyzing and classifying said impurities as soluble impurities, insoluble impurities and bubbles, based on said obtained relationships;

wherein, when the impurities in the liquid are to be measured separately, the light modulation frequency $\omega$ is determined such that it satisfies:

$$\omega \gtrsim 3h/\rho_S C_{P_S} d_c,$$

where $\rho_S$ represents the specific weight of impurities to be measured; $C_{P_S}$ represents the specific heat of the impurities; $d_c$ represents the radius of the particles; and h represents the heat transfer coefficient from the particles to the liquid; and wherein the impurities are detected and classified into soluble impurities, insoluble impurities and bubbles on the basis of the phase of the photoacoustic signals.

3. A method for analyzing impurities in liquid according to claim 2, wherein, when the phase $\theta$ of the photoacoustic signals with respect to the phase of the intensity-modulated light, with which the liquid to be measured is irradiated, satisfies:

$$\theta = 0,$$

it is determined that bubbles are mixed therein, when $$\theta = \phi_Q,$$

where $\phi_Q$ indicates the phase delay due to the propagation of the photoacoustic signals, it is determined that soluble impurities are mixed therein; and when $$\theta = \phi_Q + \phi_D,$$

where $\phi_D$ is the phase delay due to the time required for heat transference from the impurities to the liquid, it is determined that insoluble impurities are mixed therein.

4. A method for analyzing impurities in a liquid according to claim 3, wherein inpurities are classified into soluble impurities, insoluble impurities and bubbles on the basis of the phase $\theta$ of the photoacoustic signals and the concentration of each class of impurity is obtained on the basis of the intensity of the photoacoustic signals.

5. A method for analyzing impurities in a liquid according to claim 4, wherein, when the phase of $\theta$ of the photoacoustic signals is represented by:

$$\theta = \phi_Q + \phi_D,$$

the mean particle radius of the insoluble impurities is calculated on the basis of the value of $\phi_D$.

6. An apparatus for analyzing impurities in a liquid comprising:
   a light source;
   at least one light modulator transforming light from said light source into intensity-modulated light having an arbitrary constant frequency;
   at least one cell, containing a liquid to be measured, disposed at a position where it is irradiated with said intensity-modulated light so as to induce the impurities to generate photoacoustic signals in the liquid;
   at least one phase detection device for detecting the phase of the photoacoustic signals coming from the cell;
   a calculating device for analyzing impurities in the liquid on the basis of information coming from the phase detection device; and
   a control device for controlling the modulation frequency (light modulation frequency $\omega$) of the intensity-modulated light in said light modulator.

7. An apparatus for analyzing impurities in a liquid according to claim 6, wherein said phase detection device detects photoacoustic signals having a predetermined phase set by a phase control device.

8. An apparatus for analyzing impurities in a liquid according to claim 7, wherein said control device includes said phase control device.

9. An apparatus for analyzing impurities in liquid according to claim 6, wherein said phase detection device amplifies the photoacoustic signals thus obtained and the control device further controls the phase and sensitivity of the phase detection device.

10. An apparatus for analyzing impurities in a liquid according to claim 7, wherein said phase detection device amplifies the photoacoustic signals thus obtained and the phase control device of said phase detection device controls the phase and sensitivity of the phase detection device.

11. An apparatus for analyzing impurities in a liquid according to claim 6, wherein said phase detection device further detects the intensity of the photoacoustic signals and wherein said calculating device for analyzing impurities analyzes the kind and the amount of the impurities contained in the liquid on the basis of the phase and the intensities of the photoacoustic signals coming from said phase detection device.

12. An apparatus for analyzing impurities in a liquid according to claim 11, wherein, when insoluble impurities are detected in the liquid to be measured, said calculating device calculates the radius of the impurities on the basis of the phase of the photoacoustic signals.

13. An apparatus for analyzing impurities in a liquid according to claim 6, wherein, when the total amount of the impurities is to be measured, said control device controls said light modulator and said phase detection device such that the light modulation frequency $\omega$ of said light modulator satisfies:

$$\omega << 3h/\rho_S C_{Ps} d_c$$

where $\rho_S$ represents the specific weight of impurities to be measured; $C_{Ps}$ represents the specific heat of the impurities; $d_c$ represents radius of the impurities; and h represents the heat transfer coefficient from the impurities to the liquid; and
   wherein, the phase $\theta$ of the phase detection device for detecting the phase of the photoacoustic signals satisfies:

$$\theta = \phi_Q,$$

where $\phi_Q$ represents the phase delay due to the propagation of the photoacoustic signals.

14. An apparatus for analyzing impurities in a liquid according to claim 6, wherein, when impurities in the liquid are to be measured separately and classified into soluble impurities, insoluble impurities and bubbles, said control device controls said light modulator such that the light modulation frequency $\omega$ of said light modulator satisfies:

$$\omega \gtrsim 3h/\rho_S C_{Ps} d_c,$$

where $\rho_S$ represents the specific weight of impurities to be measured; $C_{Ps}$ represents the specific heat of the impurities; $d_c$ represents the radius of the impurities; and h represents the heat transfer coefficient from the impurities to the liquid.

15. An apparatus for analyzing impurities in a liquid according to claim 12, wherein, when impurities in the liquid are to be measured separately and classified into soluble impurities, insoluble impurities and bubbles, said control device controls said light modulator such that the light modulation frequency $\omega$ of said light modulator satisfies:

$$\omega \gtrsim 3h/\rho_S C_{Ps} d_c,$$

where $\rho_S$ represents the specific weight of impurities to be measured; $C_{Ps}$ represents the specific heat of the impurities; $d_c$ represents the radius of the impurities; and h represents the heat transfer coefficient from the impurities to the liquid.

16. An apparatus for analyzing impurities in a liquid according to claim 14, wherein said phase detection device further detects the intensity of the photoacoustic signals,
   wherein said calculating device calculates the kind and the amount of the impurities contained in the liquid on the basis of the phase and the intensity of the photoacoustic signals coming from said phase detection device, and
   wherein, when insoluble impurities are detected in the liquid, said calculating device calculates the radius of said insoluble impurities.

17. An apparatus for analyzing impurities in a liquid according to claim 15, wherein said phase detection device further detects the intensity of the photoacoustic signals and,
   wherein said calculating device calculates the kind and the amount of the impurities contained in the liquid on the basis of the phase and the intensity of the photoacoustic signals coming from said phase detection device, and wherein, when insoluble impurities are detected in the liquid, said calculating device calculates the radius of said insoluble impurities.

18. An apparatus for analyzing impurities in a liquid according to claim 16, further comprising a display device for displaying the kind and the amount of the impurities as well as the radius of the insoluble impurities.

19. An apparatus for analyzing impurities in a liquid according to claim 9, wherein said phase detection device is a lock-in amplifier.

20. An apparatus for analyzing impurities in a liquid according to claim 10, wherein said phase detection device is a lock-in amplifier.

21. An apparatus for analyzing impurities in a liquid according to claim 19, wherein, said light modulator is a photoacoustic modulator and further comprising an oscillator disposed between said light modulator and said control device, such that the light modulation frequency of said light modulator is controlled by said control device in accordance with an oscillation frequency of said oscillator, said oscillator providing reference signals to said lock-in amplifier.

22. An apparatus for analyzing impurities in a liquid according to claim 20, wherein, said light modulator is a photoacoustic modulator and further comprising an oscillator disposed between said light modulator and said control device, such that the light modulation frequency of said light modulator is controlled by said control device in accordance with an oscillation frequency of said oscillator, said oscillator providing reference signals to said lock-in amplifier.

23. An apparatus for analyzing impurities in a liquid according to claim 6, further comprising a plurality of sets, each of which consists of a light modulator, a cell, and a phase detection device for analyzing photoacoustic signals, arranged in parallel to each other such that a light beam generated by said light source enters the cell of each of the sets, wherein the light modulation frequencies for the light modulators being so controlled that they are different from each other; and wherein the liquid to be measured flows through the cells one after another.

24. An apparatus for analyzing impurities in a liquid according to claim 23, wherein two light modulators, two cells, and two phase detection devices are disposed in parallel to comprise first and second analyzing sets, respectively;

the light modulation frequency $\omega_1$ of said first analyzing set being controlled such that it satisfies:

$$\omega_1 << 3h/\rho_S C_{P_S} d_c,$$

where $\rho_S$ represents the specific weight of the impurities to be measured; $C_{P_S}$ represents the specific heat of the impurities; $d_c$ represents the radius of the impurities; and h represents the heat transfer coefficient from the impurities to the liquid; the phase $\theta$ of the phase detection device for detecting the phase of the photoacoustic signals being set such that it satisfies:

$$\theta = \phi_Q,$$

where $\phi_Q$ indicates the phase delay due to the propagation of the photoacoustic signals;

and the light modulation frequency $\omega_2$ for said second analyzing set being controlled such that it satisfies:

$$\omega_2 > 3h/\rho_S C_{P_S} d_c.$$

25. An apparatus for analyzing impurities in a liquid according to claim 23, further comprising a light distributing device disposed between said light source and said light modulators such that light emitted by said light source is split into a plurality of light beams, wherein one of said plurality of light beams enters one of said light modulators, respectively.

26. An apparatus for analyzing impurities in a liquid according to claim 24, further comprising a light distributing device disposed between said light source and said light modulators such that light emitted by said light source is split into a plurality of light beams, wherein one of said plurality of light beams enters one of said light modulators, respectively.

27. An apparatus for analyzing impurities in a liquid according to claim 25, in which said light distributing device comprises a beam splitter and a mirror.

28. An apparatus for analyzing impurities in a liquid according to claim 26, in which said light distributing device comprises a beam splitter and a mirror.

29. An apparatus for analyzing impurities in liquid according to claim 23, wherein the number of analyzing sets is greater than two and said light distributing device comprises a beam splitter, at least one half mirror, and a mirror.

30. An apparatus for analyzing impurities in a liquid according to claim 23, wherein three light modulators, three cells and three phase detection devices are disposed in parallel to comprise first, second and third analyzing sets, respectively;

the light modulation frequency $\omega_1$ of said first analyzing set being controlled such that it satisfies:

$$\omega_1 << 3h/\rho_S C_{P_S} d_c,$$

where $\rho_S$ represents the specific weight of impurities to be measured; $C_{P_S}$ represents the specific heat of the impurities; $d_c$ represents the radius of the impurities; and h represents the heat transfer coefficient from the impurities to the liquid;

the light modulation frequency $\omega_2$ of the second and third analyzing sets being controlled that it satisfies:

$$\omega_2 \gtrsim 3h/\rho_S C_{P_S} d_c;$$

for the first and second analyzing sets, the phase $\theta$ of the phase detection device for detecting the phase of the photoacoustic signals being set such that is satisfies:

$$\theta = \phi_Q,$$

where $\phi_Q$ indicates a phase delay due to propagation of the photoacoustic signals;

whereby the concentration of the total amount of impurities is calculated on the basis of the intensity of the photoacoustic signals detected by a first phase detection device for said first analyzing set; the concentration of the soluble impurities is calculated on the basis of the intensity of the photoacoustic signals detected by a second phase detection device for said second analyzing set; and the concentration and the radius of the insoluble impurities are calculated or bubbles are detected on the basis of the intensity and the phase $\phi$ of the photoacoustic signals detected by a third phase detection device for said third analyzing set.

31. An apparatus for analyzing impurities in a liquid according to claim 30, wherein the liquid to be analyzed is ultra-pure water produced by means of an ultra-pure water production apparatus and the whole or a part of the ultra-pure water thus produced flows through the cells of said analyzing sets, one after another, such that the impurities contained in the ultra-pure water are analyzed.

32. An apparatus for analyzing impurities in a liquid according to claim 31, further comprising a commuting valve disposed between said ultra-pure water production apparatus and an ultra-pure water analyzing apparatus such that when the amount of impurities contained in the ultra-pure water exceeds a predetermined value, the ultra-pure water is returned to a suitable part in said ultra-pure water production apparatus, depending on the amount of impurities detected, and a bypass containing a degassing device disposed on piping for the ultra-pure water downstream of said ultra-pure water analyzing apparatus such that when bubbles are detected by said analyzing apparatus, the ultra-pure water is degassed by said degassing device.

33. An apparatus for analyzing impurities in a liquid according to claim 31, wherein said light source is a carbon dioxide gas laser device.

34. An apparatus for analyzing impurities in a liquid according to claim 30, wherein the liquid to be analyzed is industrial waste water, which flows through the cells of said analyzing sets one after another such that the impurities contained in the industrial waste water are analyzed.

35. A method for analyzing impurities in a liquid comprising the steps of:

modulating light at a constant modulation frequency $\omega$ so as to generate intensity-modulated light having an intensity which varies at a constant frequency;

irradiating a liquid to be measured with said intensity modulated light so as to induce impurities in said liquid to generate photoacoustic signals in said liquid;

detecting the phase of said photoacoustic signals;

obtaining relationships between the modulation frequency of said intensity modulated light, the phase of said intensity modulated light, and the phase of said photoacoustic signals; and analyzing and classifying said impurities as soluble impurities, insoluble impurities and bubbles, based on said obtained relationships.

36. A method for analyzing impurities in a liquid according to claim 35, wherein the liquid to be measured is ultra-pure water.

* * * * *